United States Patent [19]

Horrobin

[11] Patent Number: 5,380,757
[45] Date of Patent: Jan. 10, 1995

[54] METHOD OF TREATING VULVAR DYSTROPHY AND VAGINAL DRYNESS

[75] Inventor: David F. Horrobin, Surrey, England

[73] Assignee: Scotia Holdings plc, Surrey, England

[21] Appl. No.: 61,110

[22] Filed: May 14, 1993

[30] Foreign Application Priority Data

May 27, 1992 [GB] United Kingdom ................. 9211229

[51] Int. Cl.⁶ ............................................. A61K 31/20
[52] U.S. Cl. .................................................. 514/560
[58] Field of Search ......................................... 514/560

[56] References Cited

U.S. PATENT DOCUMENTS

| | | | |
|---|---|---|---|
| 4,681,896 | 7/1987 | Horrobin | 514/552 |
| 5,059,622 | 10/1991 | Sears | 514/549 |
| 5,145,686 | 9/1992 | Horrobin et al. | 424/677 |

FOREIGN PATENT DOCUMENTS 0085579  8/1983  European Pat. Off. .

OTHER PUBLICATIONS

Robinson; Can. Med. Assoc. J., vol. 140, No. 6, 1989; "Premenstrual Syndrome: Current Knowledge and Management"; pp. 605–611.

Bonacossa et al.; Prostaglandins, vol. 23, No. 1, 1982; "Effect of Corticosterone . . . "; pp. 113–128.

Ney; Med. Hypotheses, vol. 20, No. 2, Jun. 1986; "The Intravaginal Absorption of Male Generated Hormones and Their Possible Effect on Female Behaviour"; Abstract.

European Search Report, Sep. 1993.

Primary Examiner—Marianne M. Cintins
Assistant Examiner—Kimberly R. Jordan
Attorney, Agent, or Firm—Nixon & Vanderhye

[57] ABSTRACT

Gamma-linolenic (GLA) and/or dihomo-gamma-linolenic acid (DGLA) may be used in the treatment of vulvar dystrophy and/or vaginal dryness. Other essential fatty acids of the n-6 or n-3 series may also be used in association with GLA and/or DGLA.

8 Claims, No Drawings

METHOD OF TREATING VULVAR DYSTROPHY AND VAGINAL DRYNESS

The invention relates to the treatment of vulvar dystrophy and related disorders.

THE DISORDERS

The vulvar dystrophies are a common group of disorders in which various parts of the vulva atrophy or become dystrophic. The dystrophies have been the subject of many attempts at classification, the complexities of which reflect the difficulties of categorising precisely the limits of each type. The latest classification proposed by the International Society for the Study of Vulval Disease divides the dystrophies into just three groups:

1. Squamous cell hyperplasia
2. Lichen sclerosus
3. Other dermatoses

Even with this simplified classification, however, there is considerable overlapping between the syndromes. For example, while lichen sclerosus is a predominantly atrophic condition, 27-35% of women with lichen sclerosus have been reported also to show features of squamous cell hyperplasia, in which areas of the vulva are thickened and hyperplastic.

From the patients point of view, the main problem is undoubtedly pruritus, the severity of which may range from the mild to the uncontrollable and disabling. There is also often loss of normal vulval and vaginal secretions, particularly during sexual activity resulting in difficulty with or an inability to achieve intercourse.

While the vulvar dystrophies are undoubtedly common after the menopause, they can occur at any time of life, even during childhood.

Treatment is often unsatisfactory. Local hygiene and antipruritic ointments and creams may be beneficial but topical preparations containing either glucocorticoids or testosterone, the male sex hormone, are usually required. While these hormone based preparations are often effective, the glucocorticoids when used for long periods carry a serious risk of producing atrophy and thinning of the epithelium, while the testosterone preparations can produce clitoral enlargement or other masculinisation.

ESSENTIAL FATTY ACIDS

The cause of the vulvar dystrophies is unknown. However we have recently made observations which suggest that abnormal essential fatty acid metabolism is involved. The main essential fatty acid in the diet is linoleic acid. Deficiency of linoleic acid in animals produces atrophy and hyperkeratosis of the skin although there are no reports in the literature of the effects of essential fatty acids on the vulva. However, in Western countries any broad dietary deficiency of EFAs is exceedingly unlikely. The daily requirement for linoleic acid is around 1% of total calorie intake, or of the order of 2-3 g for an adult. In fact, intakes/day are usually in the 10-30 g range and nutritional deficiency of EFAs will occur only in abnormal situations, such as in individuals who have lost most of their intestinal function, or who are being fed by total parenteral nutrition without adequate EFA supplementation.

The pathways of conversion of the main series of polyunsaturated fatty acids in the body are as in Table 1 below:

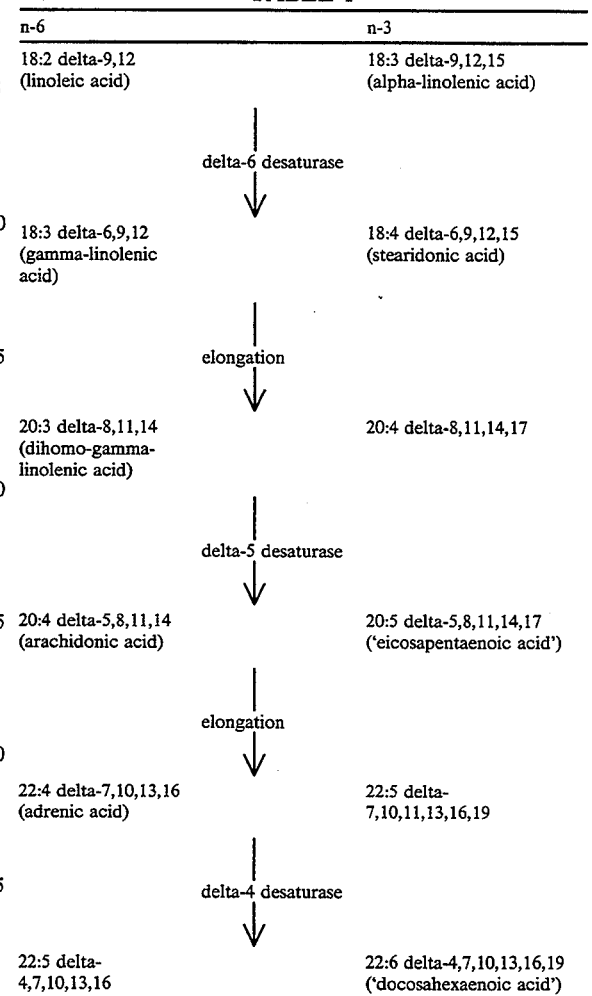

TABLE 1

The above pathways are not normally reversible nor, in man, are n-3 and n-6 series acids inter-convertible.

The acids, which in nature are of the all-cis configuration, are systematically named as derivatives of the corresponding octadecanoic, eicosanoic or docosanoic acids, e.g. delta-9, 12-octadecadienoic acid or delta-4, 7, 10, 13, 16, 19 docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexaenoic acid as such are also used. The alpha isomer of linolenic acid was characterised earlier than gamma-linolenic acid and reference in the literature simply to linolenic acid, especially in the earlier literature, is to the alpha-acid.

As is clear from the above, in order to be effectively used by the body, linoleic acid must be metabolised first to gamma-linolenic acid (GLA) and then to dihomo-gamma-linolenic acid (DGLA) and further metabolites. While conversion of GLA to DGLA is rapid and two fatty acids therefore have similar actions in vivo, the conversion of linoleic acid to GLA is relatively slow and rate-limiting, particularly in a number of disease states. For example in atopic eczema, in diabetes, and in women with breast pain and premenstrual syndrome, the formation of GLA may be slower than normal and as a result, even though linoleic acid intake may be adequate, considerable benefit is to be gained from consuming GLA directly. One good source of GLA is evening primrose oil, and GLA as evening primrose oil is licensed as a pharmaceutical in the U.K. for the treatment of breast pain.

DISLOSURE OF THE INVENTION

In a series of eight women, who were taking GLA for the treatment of either premenstrual syndrome or breast pain, and who also had vulvar dystrophy in the form either of squamous cell hyperplasia or of lichen sclerosus, there was a dramatic effect on the vulvar dystrophy. Pruritus was reduced or abolished, the appearance of the epithelium moved towards normal, and vaginal and vulval secretions increased allowing normal sexual intercourse. Other women suffering from vaginal dryness without vulvar dystrophy also reported an increase in vaginal secretion. These entirely unexpected effects of GLA suggest that it can be utilised for the treatment of both vulvar dystrophy and vaginal dryness, the latter occurring either alone or in association with vulvar dystrophy. Although DGLA has not been tested, GLA is rapidly converted to DGLA and it is anticipated that DGLA will have a similar effect. Other fatty acids of either the n-6 and n-3 series may optionally be administered in association with GLA or DGLA. Such EFAs include arachidonic acid, eicosapentaenoic acid, stearidonic acid and docosahexaenoic acid.

The invention thus provides a method of treatment of vulvas dystrophy and/or vaginal dryness, wherein there is administered GLA and/or DGLA, optionally in association with other EFAs of the n-6 or n-3 series.

The invention further provides the use of GLA and/or DGLA, optionally in association with other EFAs of the n-6 or n-3 series, in the preparation of a medicament for the treatment of vulvar dystrophy and/or vaginal dryness.

The invention also provides a medicament for use in the treatment of vulvar dystrophy and/or vaginal dryness, which medicament comprises GLA and/or DGLA, optionally in association with other EFAs of the n-6 or n-3 series.

Preferably, the GLA and/or GLA is presented for systemic administration of 1 mg to 10 g/day more preferably 100 mg to 5 g/day most preferably 300 mg to 2 g/day of the or each acid.

In particular applications, the GLA and/or DGLA may for example be presented for local administration as creams, lotions, ointments, pessaries or suppositories or other appropriate formulations containing from 0.01% to 50% of GLA or DGLA by weight, more preferably 0.1% to 20%, most preferably 1% to 5%, or as a topical formulation containing by weight 0.01 to 30%, more preferably 0.1 to 20% most preferably 1% to 10%, suited to administration of up to 5 g GLA and/or DGLA daily.

DIETARY COMPOSITIONS

The invention is chiefly described in terms of methods of treatment and pharmaceutical compositions, but it will be understood that the gamma-linolenic and other EFAs, being in the nature of dietary supplements, can be incorporated in a dietary margarine or other foodstuff and such are to be understood as within the term pharmaceutical composition or medicament herein (including in the claims) when for the purposes set out.

DERIVATIVES OF EFAs

The acids may be used as such or as pharmaceutically acceptable and physiologically equivalent derivatives as, for example, detailed below for GLA and DGLA, and reference to any of the acids is to be taken as including reference to the acids when in the form of such derivatives. Equivalence is demonstrated by entry into the pathway quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et at, page 23, "Analysis of Lipids and Lipoporteins" Ed Perkins, American Oil Chemists Society, Champaign, Ill., U.S.A.

FORMS AND SOURCES OF GAMMA-LINOLENIC AND OTHER ACIDS

Convenient physiologically equivalent derivatives of GLA and DGLA for use according to the invention as with the other acids, includes salt, amides, esters including glyceride esters and alkyl (e.g. $C_1$ to $C_4$) esters, cholesterol esters and phospholipids, and any other appropriate forms.

If desired, pharmaceutical compositions may be produced for use in the invention by associating the natural or synthetic acids, as such or as derivatives, with an acceptable pharmaceutical vehicle. It is, however, at present convenient to provide at least GLA in the form of an available oil having a high GLA content, hence reference to "oils" herein.

One source of oils currently available is the seed of evening primrose species such as *Oenothera biennis L.* and *Oenothera lamarckiana*, the oil extract therefrom containing about 8% GLA and about 72% linoleic acid in the form of their glycerides, together with other glycerides (percentages based on total fatty acids). Other sources of GLA are borage species such as *Borago officinalis* which, though current yield per acre is low, provide a richer source than Oenothera oil. Oils from the seeds of members of the Ribes family are also often rich in GLA. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:
Palmitate 6.15
Stearate 1.6
Oleate 10.15
Linoleate 72.6
Gamma-linolenate 8.9

The seed oil extracts referred to above can be used as such or can, for example, if desired, be fractionated to yield an oily composition containing the triglycerides of gamma-linolenic and linoleic acids as the main fatty acid components, the gammalinolenic acid content being, if desired, a major proportion. Seed oil extracts appear to have a stabilising effect upon DGLA if present.

SOURCES OF OTHER ACIDS

DGLA can be prepared by chemical synthesis or by fungal fermentation. For the higher n-6 acids, natural sources of 22:4 and 22:5 n-6 acids include adrenal glands (22:5) and kidneys (22:4) obtained from slaughter houses, which also give AA sources, and 22:4 in the fat of the American Snapping Turtle.

The n-3 acids are available from marine oils, particularly the 20:5 n-3 and 22:6 n-3 acids, and more recently from microbial fermentation. They can be isolated from these sources by, for example, saponifaction under mild non-oxidising conditions followed by preparative gas liquid chromatography. Synthesis is difficult but not impossible and provides another source.

PHARMACEUTICAL PRESENTATION

As discussed above, the compositions are conveniently in a form suitable for oral, topical, vaginal, rectal or parenteral administration in a suitable pharmaceutical vehicle, as very well known generally for any particular kind of preparation. Thus, for example, tablets, capsules, ingestible liquid or powder preparations can be prepared as required, and topical preparations also when the gamma-linolenic acid or other acids are absorbed through the skin or vulval or vaginal tissues. Injectable solutions of hydrolysed Oenothera oil may be prepared using albumin to solubilise the free acid.

Advantageously, a preservative is incorporated into the preparation. Alphatocopherol in concentration of about 0.1% by weight has been found suitable for the purpose and is one of a number of possible stabilisers well known in the field and including also for example ascorbyl palmitate and stearate.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The GLA or DGLA may be administered by any appropriate route, oral, rectal, vaginal, parenteral or topical.

The invention is further illustrated by the following examples.

EXAMPLES

1. Oral administration of GLA and/or DGLA, 1 mg to 10 g/day, preferably 100 mg to 5 g, very preferably 300 mg to 2 g in any appropriate form such as:
   a. Soft gelatin capsules containing 50 mg or 100 mg of GLA or DGLA in the form of evening primrose oil, borage oil, blackcurrant seed oil or other form including free fatty acid, or lithium, sodium, potassium, zinc, magnesium, calcium, or other salt, or glycerides, or phospholipids, or amides or any other pharmacologically acceptable form that can be demonstrated to raise the levels of GLA or DGLA in the blood or epithelium.
   b. Hard gelatin capsules with EFAs as above.
   c. Hard or soft gelatin capsules containing 500 mg purified GLA or DGLA.
   d. Powders made by any appropriate method and which can be taken as such, tabletted, or packed in hard gelatin capsules or any other appropriate form.
   e. Liquids in any appropriate pharmaceutical format including oils, whips, foams, cream; aerosols, etc.
2. Parenteral administration of GLA and/or DGLA in the dose specified in 1 above by subcutaneous, intramuscular or intravenous infusion or injection.
3. Administration of GLA and/or DGLA per rectum or per vaginam or to the vulva by the use of creams, ointments, lotions, pessaries or suppositories containing from 0.01% to 50% of GLA or DGLA by weight, preferably from 0.1 to 20%, more preferably from 1% to 5%, with the aim of providing up to 5 g/day of GLA and/or DGLA.
4. Topical administration of ointments, creams, lotions, sticks, salves or other formulations which contain by weight from 0.001 to 30%, preferably from 0.1 to 20%, more preferably from 1% to 10% GLA and/or DGLA in appropriate form, including native oils, glycerides, free fatty acids, salts, phospholipids, amides, or any other derivative capable of elevating GLA or DGLA in the skin or the blood, with the aim of providing up to 5 g/day of GLA and/or DGLA.
5. Preparations as in 1–4 in which the GLA or DGLA are associated with other essential fatty acids such as arachidonic acid, stearidonic acid, eicosapentaenoic acid, docosapentaenoic acid (22:5n-3) or docosahexaenoic acid.

I claim:

1. Method of treating vulvar dystrophy, vaginal dryness or both comprising administering to a woman requiring such treatment from 1 mg to 10 g/day of GLA, DGLA, or both, optionally in association with other EFAs of the n-6 or n-3 series.

2. The method according to claim 1 wherein the GLA or DGLA is presented for systemic administration of from 100 mg to 5 g/day.

3. The method according to claim 2 wherein the amount of GLA or DGLA is from 300 mg to 2 g/day.

4. The method according to claim 1 wherein the GLA or DGLA is administered in the form of a cream, ointment, lotion, pessary or suppository formulation containing from 0.001% to 50% of GLA or DGLA by weight suited to the administration of up to 5 g GLA and/or DGLA daily.

5. The method of claim 4 wherein the formulation contains from 0.1% to 20% GLA or DGLA.

6. The method of claim 5 wherein the formulation contains from 1% to 5% GLA or DGLA.

7. The method according to claim 1, wherein the GLA or DGLA is applied topically as a topical formulation containing from 0.001% to 30% by weight GLA or DGLA suited to the administration of up to 5 g GLA or DGLA daily.

8. The method of claim 13 wherein the formulation contains from 1% to 10% GLA or DGLA.

* * * * *